(12) United States Patent
Long

(10) Patent No.: US 10,531,936 B2
(45) Date of Patent: Jan. 14, 2020

(54) DENTAL DEVICE

(71) Applicant: Innovative Materal and Devices, Inc., Shanghai (CN)

(72) Inventor: Xiaoping Long, Shanghai (CN)

(73) Assignee: INNOVATIVE MATERIAL AND DEVICES, INC., Jia Ding District, Shanghai (CN)

( * ) Notice: Subject to any disclaimer, the term of this patent is extended or adjusted under 35 U.S.C. 154(b) by 0 days.

(21) Appl. No.: 15/864,517

(22) Filed: Jan. 8, 2018

(65) Prior Publication Data

US 2019/0209270 A1     Jul. 11, 2019

(51) Int. Cl.
*A61C 7/28*     (2006.01)

(52) U.S. Cl.
CPC .................... *A61C 7/287* (2013.01)

(58) Field of Classification Search
CPC .... A61C 7/28; A61C 7/30; A61C 7/34; A61C 7/148; A61C 7/287; A61C 2201/007
USPC ................................. 433/8, 10, 13
See application file for complete search history.

(56) References Cited

U.S. PATENT DOCUMENTS

| | | | | |
|---|---|---|---|---|
| 5,464,347 A * | 11/1995 | Allesee | ..................... | A61C 7/12 433/16 |
| 5,466,151 A * | 11/1995 | Damon | ................... | A61C 7/146 433/10 |
| 5,820,370 A * | 10/1998 | Allesee | ..................... | A61C 7/12 433/8 |
| 6,071,118 A * | 6/2000 | Damon | ................... | A61C 7/287 433/10 |
| 7,416,408 B2 | 8/2008 | Farzin-Nia et al. | | |
| 7,704,072 B2 | 4/2010 | Damon | | |
| 7,857,618 B2 * | 12/2010 | Abels | ....................... | A61C 7/12 433/11 |
| 2005/0239012 A1 * | 10/2005 | Bathen | ................... | A61C 7/287 433/10 |
| 2010/0304321 A1 * | 12/2010 | Patel | ....................... | A61C 7/20 433/9 |
| 2012/0270175 A1 * | 10/2012 | Huge | ....................... | A61C 7/34 433/14 |

* cited by examiner

*Primary Examiner* — Wade Miles
*Assistant Examiner* — Matthew P Saunders
(74) *Attorney, Agent, or Firm* — Sughrue Mion, PLLC

(57) ABSTRACT

A self-ligating orthodontic bracket for installation on a tooth includes a bracket body defining an archwire slot, the bracket body including a lingual surface configured to be mounted on a tooth. One or more posts extend outward from a first surface of the bracket body, and a ligating member is moveable along the first surface between a first, open position which allows access to the archwire slot, and a second, closed position which restricts access to the archwire slot. The ligating member includes projections to contact the one or more posts and maintain the ligating member in at least one of the open position, closed position, and a transition movement between the open position and the closed position.

18 Claims, 6 Drawing Sheets

DENTAL DEVICE

TECHNICAL FIELD

The present invention relates generally to the field of orthodontic brackets, and particularly to ligating brackets providing tooth corrective treatment.

BACKGROUND

Orthodontic treatment is often directed to correcting the alignment or position of teeth, for example dental crowding, flaring, irregularity in tooth alignment, unpleasing tooth appearance, difficulty in chewing, among other issues.

One tool employed by orthodontists for these purposes is the orthodontic bracket. An orthodontic bracket attaches to a tooth, and holds an orthodontic archwire. Attachment of the bracket to the tooth transmits a force to the tooth when a resilient orthodontic archwire is bent or twisted, and then brought to engage with the bracket. A mechanical force system may thus be constructed to generate force sequentially to the teeth, thus directing the teeth to their desired positions.

Orthodontic brackets engage the archwire into an archwire slot by ligation using elastomeric or wire ligatures wrapped around protrusions (e.g., "wings") of the bracket. Ligatures or some form of fastening means are utilized to secure the archwire in the bracket slot to prevent the archwire from being dislodged and thus to maintain the position of the active archwire around the dental arch.

In existing bracket designs, ligation generates a non-homogeneous force during sliding, and does not provide a clear force-feedback indication to the installer of the bracket that the archwire has reached a secure position in the bracket. Another drawback of conventional designs is that deformation of the bracket and/or archwire may result in difficulties installing or securing the bracket by ligation.

Advantages of an improved orthodontic bracket design as described herein will be more readily understood upon consideration of the following detailed description of the invention taken in conjunction with the accompanying drawings.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

An improved orthodontic bracket is described that provides a ligating member force that is stable throughout a sliding motion between an open and closed position. In particular, ligating force drop is mitigated when the ligating member arrives at its opened and closed positions. This makes it easier for the user to identify whether a stop position (open or closed) is achieved.

Figure 1A:
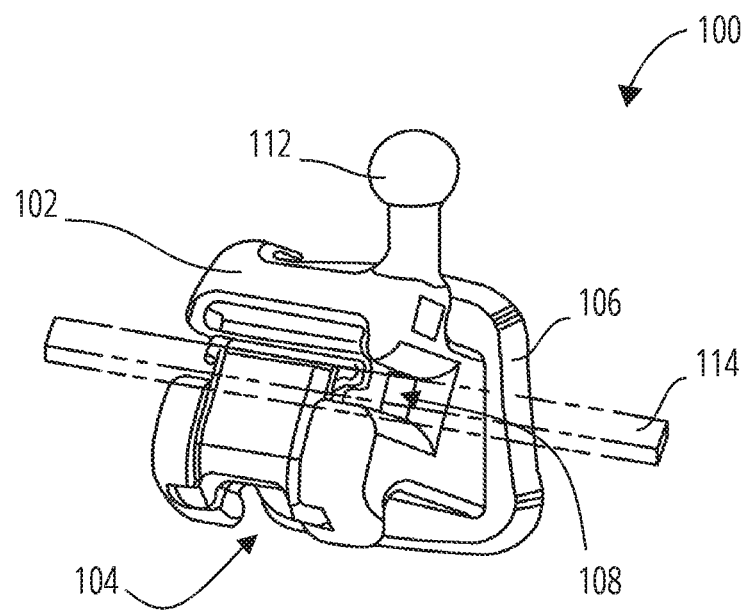
FIGS. 1A and 1B illustrate an orthodontic bracket 100 in accordance with one embodiment.
Figure 1B:
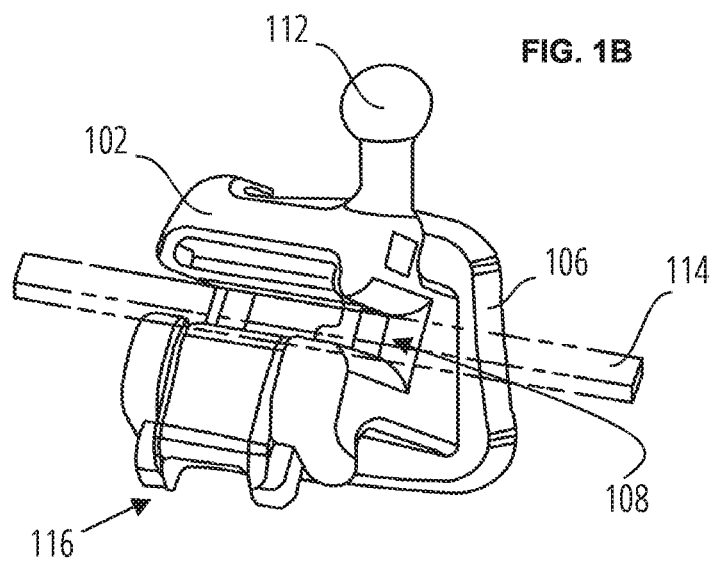

Referring to FIGS. 1A and 1B, an orthodontic bracket 100 comprises a bracket body 102, a ligating member dock 104, a mesh 106 (e.g., lingual surface), a main slot 108, and a hook 112.

The mesh 106 is pressed against a tooth, and the orthodontic bracket 100 is aligned on the tooth. A ligating member 116 is slid into the ligating member dock 104, moving from an open position to a closed position (as further illustrated in FIG. 5A, FIG. 5B, and FIG. 6), securing the archwire 114 in the main slot 108. Slot 108 can be in the range of approximately 0.018"-0.022" wide and preferably 0.018," 0.021" or 0.022" wide.

Figure 2A:
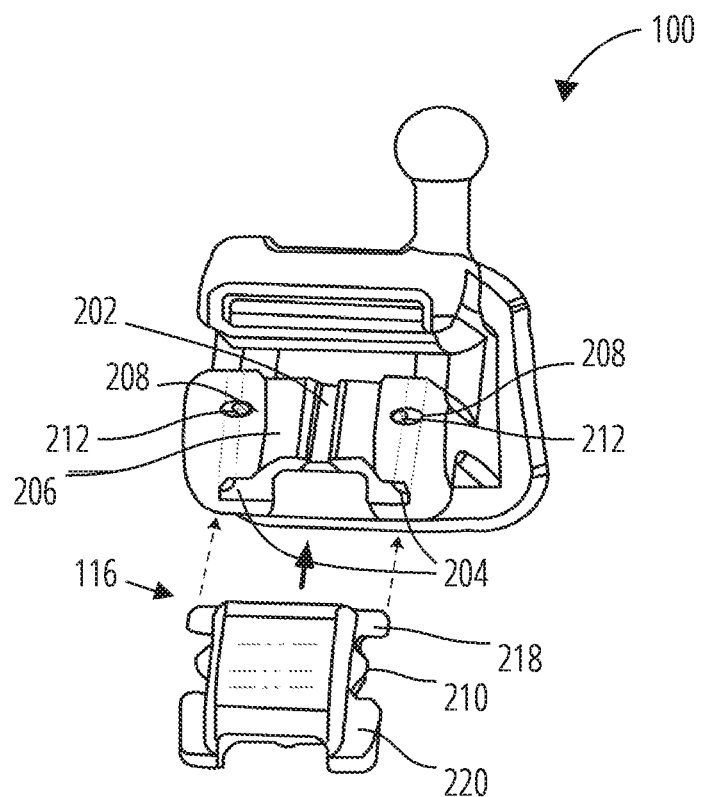
FIGS. 2A, 2B, and 2C illustrate additional aspects of an orthodontic bracket 100 in accordance with one embodiment.
Figure 2B:
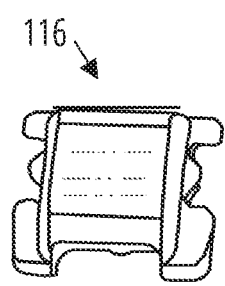
Figure 2C:
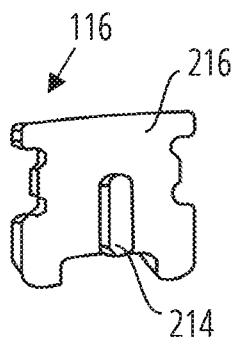
Figure 4:
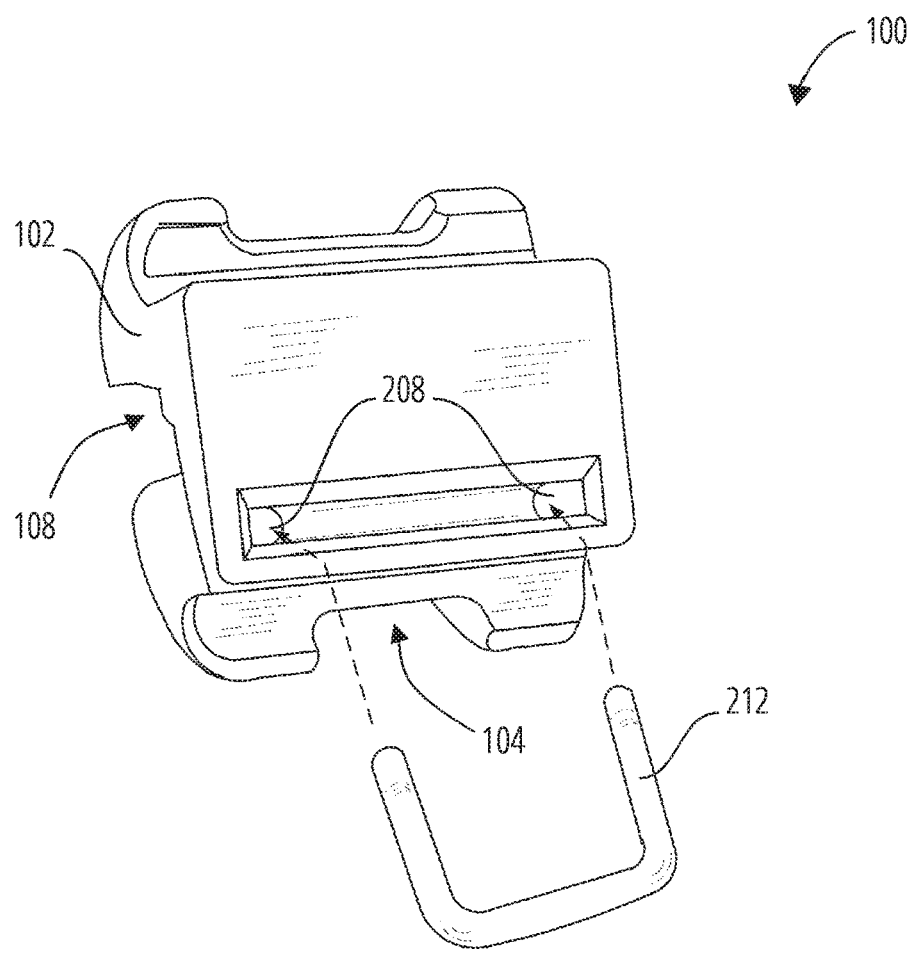
FIG. 4 illustrates an orthodontic bracket 100 in accordance with one embodiment.

The orthodontic bracket 100, and the ligating member dock 104 in particular, further comprises a leading groove 202 (see FIGS. 2A, 2B, and 2C), slot guides 204, a ligating member abutting surface 206, and holes 208 to receive one or more posts 212 (e.g., the ends of a U-shaped wire). It is noted that the holes 208 need not extend through the labial surface of the bracket body 102. As shown in FIG. 4, some embodiments receive one or more posts through holes 208 in the lingual surface of the bracket body.

Figure 5A:
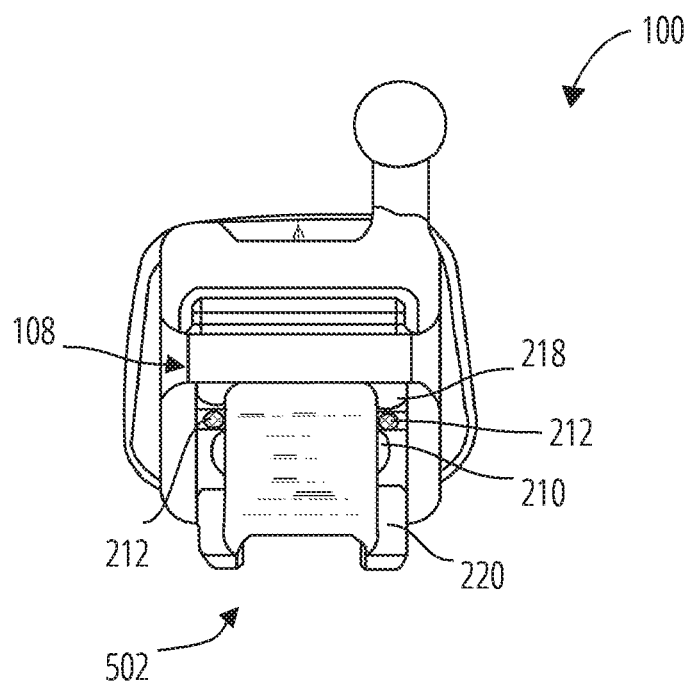
FIGS. 5A and 5B illustrate the ligating member 116 sliding in the ligating member dock 104 of the orthodontic bracket 100 in accordance with one embodiment.
Figure 5B:
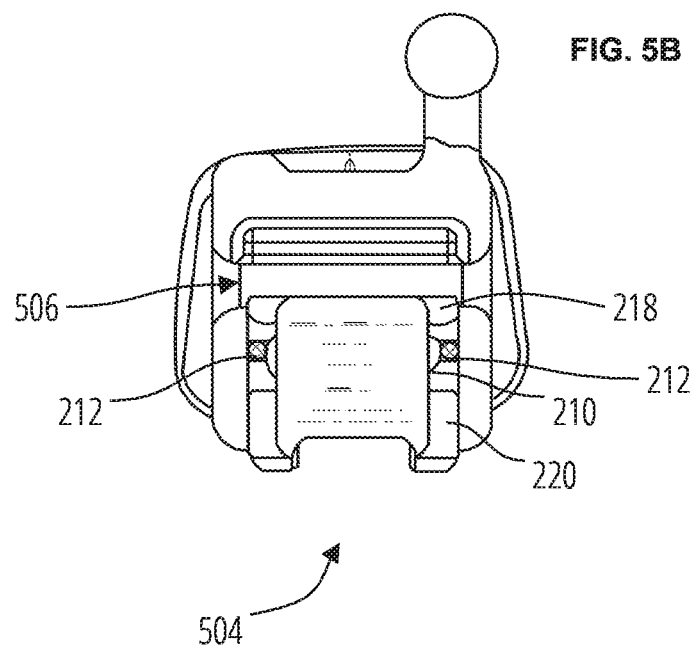
Figure 6:
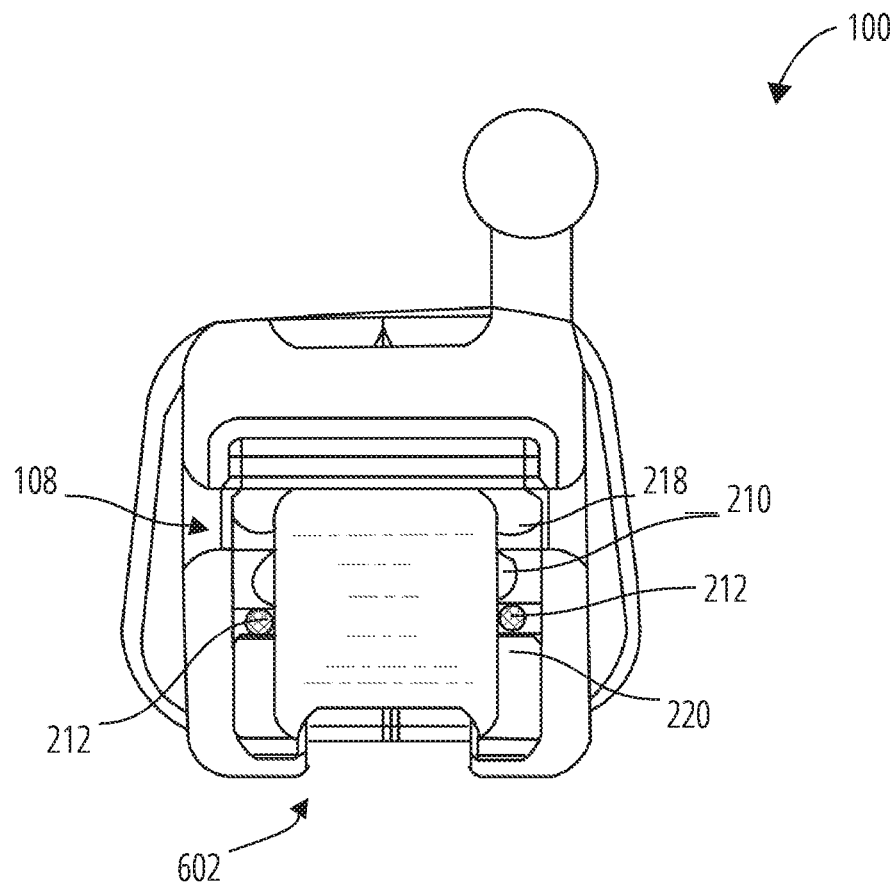
FIG. 6 illustrates the ligating member 116 in a closed position 602 in accordance with one embodiment.

As will be further illustrated in conjunction with FIG. 5A, FIG. 5B, and FIG. 6, due to the dynamic mechanical engagement between an edge profile of the ligating member 116 and the post or posts 212, in an open position 502 and closed position 602 of the ligating member 116, the posts are closer to one another than in a transition position 504 of the ligating member 116. Although illustrated in a preferred mode as ends of a U-shaped wire, the posts may also be independent posts, studs, or other mechanisms having similar properties.

The ligating member 116 is received into the ligating member dock 104. The ligating member 116 includes a leading projection 214 to engage with the leading groove 202, a bracket body abutting surface 216 to engage with the ligating member abutting surface 206, and first stopping projections 218 and second stopping projections 220. Typical materials for constructing the ligating member 116 and/or the bracket body 102 include stainless steel or hard (resistant to deformation) plastic or ceramic.

As illustrated, the edge profile of the ligating member 116 may be described as an "M" shaped cutaway, or wave profile. However, other embodiments of the ligating member 116 may utilize an edge profile more clearly described as an S or W, for example.

Figure 3:
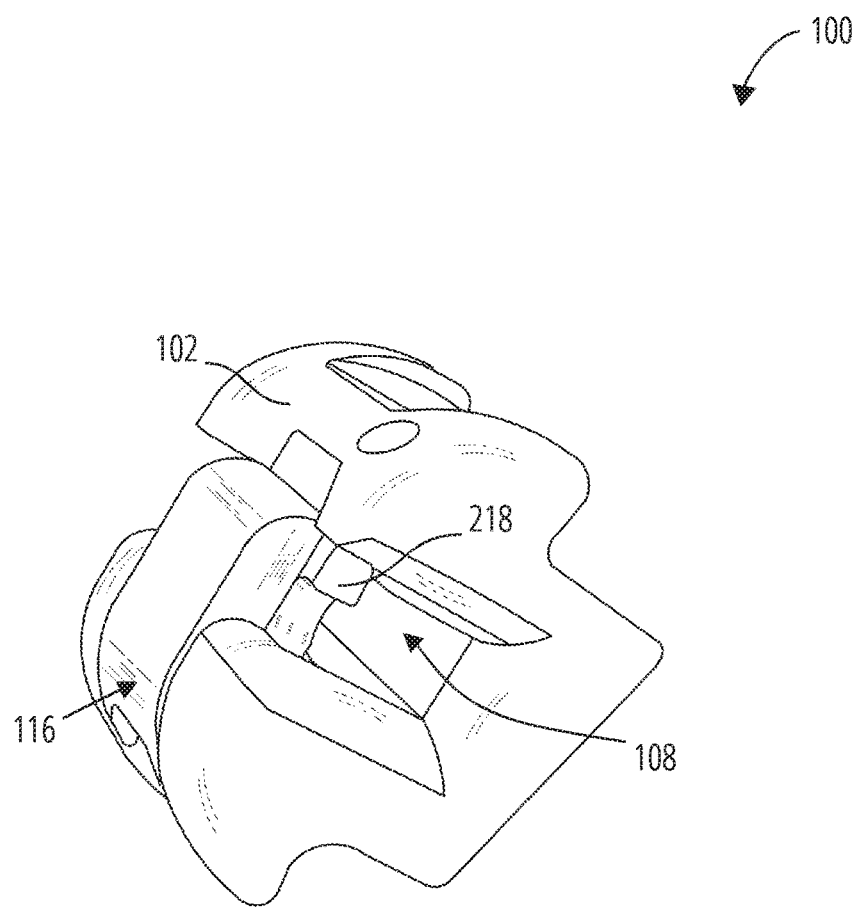
FIG. 3 illustrates an orthodontic bracket 100 in a perspective view, in accordance with one embodiment.

In FIG. 3, the ligating member 116 is illustrated in the fully closed position. When the ligating member 116 is transitioning from an open position to a closed position or vice versa, an improved dynamic mechanical engagement is made between the edge profile (e.g., a wave profile) of the ligating member 116 and a post or posts (e.g., posts 212). It is this dynamic mechanical engagement that provides an improved tactile experience for the user of the orthodontic bracket 100. The open and closed positions are more readily detected via haptic feedback to the user from the mechanical engagement of the ligating member 116 edge profile and the posts.

In various embodiments, post 212 may be constructed from materials with resistance to shape and structural fatigue from repeated deformation. Non-limiting examples of materials include nickel-titanium alloy, copper-nickel-titanium allow, memory shape alloy, steel materials, and plastic materials. Post 212 is illustrated as a U-shaped wire, but in other embodiments may be implemented as two or more individual solid wires, twisted wires, pins, or rods, for example.

Once engaged with the ligating member dock 104, the ligating member 116 slides between an open position 502, through a sliding position 504, to closed position 602. The post or posts 212 create extend outward from the ligating member abutting surface 206 of the bracket body. The ligating member 116 moves along the ligating member abutting surface 206 of the bracket body 102 between the open position 502, which allows access to the main slot 108 (archwire slot), and the closed position 602 which restricts access to the archwire slot.

The ligating member 116 includes projections (first stopping projections 218, guiding projections 210, and second stopping projections 220) configured to contact the post or posts 212 and maintain the ligating member 116 in at least one of the open position 502, the closed position 602, and a transition movement (e.g., sliding position 504) between the open position 502 and the closed position 602.

The leading projection 214 engages the leading groove 202 providing a guideway between the open position 502 and the closed position 602.

In some embodiments, the ligating member 116 includes four stopping projections at the corners (e.g., first stopping projections 218 and second stopping projections 220) extending laterally from the ligating member 116 to stop the ligating member 116 from sliding beyond the open position 502 and the closed position 602, and two guiding projections (e.g., guiding projections 210) extending laterally from the ligating member 116 to resist movement of the ligating member 116 between the open position 502 and the closed position 602. In some embodiments, for example as illustrated, the guiding projections 210 extend less laterally than the stopping projections.

The foregoing description of embodiments and examples has been presented for purposes of illustration and description. It is not intended to be exhaustive or to limit the invention to the forms described. Numerous modifications are possible in light of the above teachings. Some of those modifications have been discussed and others will be understood by those skilled in the art. The embodiments were chosen and described in order to best illustrate certain principles and various embodiments as are suited to the particular use contemplated. The scope of the invention is, of course, not limited to the examples or embodiments set forth herein, but can be employed in any number of applications and equivalent devices by those of ordinary skill in the art. Rather it is hereby intended the scope of the invention be defined by the claims appended hereto.

What is claimed is:

1. A self-ligating orthodontic bracket for installation on a tooth, comprising: a bracket body defining an archwire slot, said bracket body including a lingual surface configured to be mounted on a tooth; a wire inserted into said bracket body through said lingual surface, said wire forming a first post extending outward from a first surface of said bracket body and a second post extending outward from said first surface of said bracket body; a ligating member moveable along said first surface of said bracket body between a first, open position which allows access to the archwire slot, and a second, closed position which restricts access to the archwire slot, said ligating member having first projections configured to contact said first post and second projections configured to contact said second post, said first projections and said second projections being configured to maintain said ligating member in at least one of said open position, said closed position, and a transition movement between said open position and said closed position.

2. A self-ligating orthodontic bracket according to claim 1, said wire is a U-shaped wire.

3. A self-ligating orthodontic bracket according to claim 1, wherein at least one surface of said ligating member is formed in a W-shape.

4. A self-ligating orthodontic bracket according to claim 3, wherein at least two surfaces of said ligating member are formed in a W-shape.

5. A self-ligating orthodontic bracket according to claim 1, wherein said bracket body comprises a guideway, said ligating member slides within said guideway between said open position and said closed position, and said projections comprise four stopping projections at corners of said ligating member extending laterally from said ligating member to stop said ligating member from sliding beyond said open position and said closed position, and two guiding projections extending laterally from said ligating member to resist movement of said ligating member between said open position and said closed position.

6. A self-ligating orthodontic bracket according to claim 5, wherein said guiding projections extend less laterally than said stopping projections.

7. A self-ligating orthodontic bracket for installation on a tooth, comprising: a wire, inserted through a lingual surface of a bracket body, forming a first post extending outward from a first surface of a said bracket body and a second post extending outward from said first surface of said bracket body; a ligating member moveable along said first surface of said bracket body between a first, open position which allows access to an archwire slot, and a second, closed position which restricts access to the archwire slot, said ligating member having a first plurality of projections along a first edge profile and a second plurality of projections along a second edge profile opposing the first edge profile, said first plurality of projections being configured to contact said first post and said second plurality of projections being configured to contact said second post, said first post and said second post being closer in proximity to one another in the open and closed positions than in a position between said open and said closed positions.

8. A self-ligating orthodontic bracket according to claim 7, wherein said one or more posts are the ends of a U-shaped wire inserted into said bracket body.

9. A self-ligating orthodontic bracket according to claim 7, wherein said one or more posts are one or more solid individual wires, or twisted wires.

10. A self-ligating orthodontic bracket according to claim 7, wherein one or more posts are made from one or more of nickel-titanium alloy and copper-nickel-titanium alloy.

11. A self-ligating orthodontic bracket according to claim 7, wherein said bracket body comprises a guideway, said ligating member slides within said guideway between said open position and said closed position, and said projections comprise four stopping projections at corners of said edge profiles of said ligating member extending laterally from said ligating member to stop said ligating member from sliding beyond said open position and said closed position, and two guiding projections extending laterally from said ligating member to resist movement of said ligating member between said open position and said closed position.

12. A self-ligating orthodontic bracket according to claim 11, wherein said guiding projections extend less laterally than said stopping projections.

13. A self-ligating orthodontic bracket according to claim 7, wherein said edge profiles comprise one of a wave profile, an M profile, a W profile, or an S profile.

14. A self-ligating orthodontic bracket according to claim 8, wherein a composition of said U-shaped wire is made from at least one of nickel-titanium alloy and copper-nickel-titanium alloy.

15. A self-ligating orthodontic bracket according to claim 1, wherein said archwire slot is 0.018 inches wide.

16. A self-ligating orthodontic bracket according to claim 1, wherein said archwire slot is 0.021 inches wide.

17. A self-ligating orthodontic bracket according to claim 1, wherein said archwire slot is 0.022 inches wide.

18. A self-ligating orthodontic bracket according to claim 1, wherein the width of said archwire slot is in the range of approximately 0.018 inches to 0.022 inches wide.

* * * * *